United States Patent
Stergiopoulos et al.

(10) Patent No.: US 6,705,998 B2
(45) Date of Patent: *Mar. 16, 2004

(54) METHOD AND DEVICE FOR MEASURING SYSTOLIC AND DIASTOLIC BLOOD PRESSURE AND HEART RATE IN AN ENVIRONMENT WITH EXTREME LEVELS OF NOISE AND VIBRATIONS

(75) Inventors: Stergios Stergiopoulos, Toronto (CA); Amar Dhanantwari, Vaughan (CA); Lisa Pinto, Pickering (CA); Ronald Zachariah, Richmond Hill (CA)

(73) Assignee: Her Majesty the Queen in right of Canada, as represented by the Minister of National Defence, Ottawa (CA)

( * ) Notice: Subject to any disclaimer, the term of this patent is extended or adjusted under 35 U.S.C. 154(b) by 9 days.

This patent is subject to a terminal disclaimer.

(21) Appl. No.: 10/133,575

(22) Filed: Apr. 29, 2002

(65) Prior Publication Data

US 2002/0143259 A1 Oct. 3, 2002

Related U.S. Application Data

(63) Continuation-in-part of application No. 09/718,515, filed on Nov. 24, 2000.

(51) Int. Cl.[7] ................................................. A61B 5/02
(52) U.S. Cl. ........................ 600/493; 600/485; 600/490; 600/495
(58) Field of Search ................................ 600/485, 490, 600/493, 495, 499, 500

(56) References Cited

U.S. PATENT DOCUMENTS 4,005,701 A * 2/1977 Aisenberg et al. .......... 600/493
4,105,020 A    8/1978 Matsuoka et al.

(List continued on next page.)

OTHER PUBLICATIONS

"Adaptive Interference Canceling", Prentice Hall, Englewood Cliffs, NJ 07632, 1985, Chapter 12, pp. 335–343.

S. Stergiopoulos "Implementation of Adaptive and Synthetic–Aperture Processing Schemes in Integrated Active–Passive Sonar Systems", IEEE, vol. 86 No. 2, 358–396, Feb. 1998.

S. Stergiopoulos "Limitations on Towed–Array Gain Imposed By a Nonisotropic Ocean", Journal of Acoustic Society of America, 90(6), 3161–3172, 1991.

*Primary Examiner*—Robert L. Nasser
*Assistant Examiner*—Patricia Mallari
(74) *Attorney, Agent, or Firm*—Freedman & Associates

(57) ABSTRACT

A method and a device for measuring systolic and diastolic blood pressure and heart rate in an environment comprising extreme levels of noise and vibrations is disclosed. Blood pressure signals corresponding to the Korotkoff sounds are detected using a first acoustic sensor, or array of sensors, placed on the patient's skin over the brachial artery. A second acoustic transducer is placed on the outside of a pressure cuff the patient away for detecting noise and vibrations. Pressure is applied to the artery using the pressure cuff forcing the artery to close. The pressure is then reduced and while reducing the pressure the acoustic signals detected by the first and second acoustic sensor as well as a signal indicative of the pressure applied to the artery are provided to a processor. The signal of the first acoustic sensor is then processed using an adaptive interferer canceller algorithm with the signal of the second acoustic sensor as interferer. From the processed signal heart beat pulses are determined and relating the heart beat pulses to the pressure signal provides the systolic and diastolic blood pressure. Use of the adaptive interferer canceller provides good results for measurements performed under extreme levels of noise and vibrations such as aboard a helicopter, naval vessels, ambulances and noisy emergency rooms.

28 Claims, 7 Drawing Sheets

U.S. PATENT DOCUMENTS

| | | | |
|---|---|---|---|
| 4,295,471 A | * 10/1981 | Kaspari | 600/488 |
| 4,537,200 A | 8/1985 | Widrow | |
| 4,928,705 A | 5/1990 | Sekhar et al. | |
| 5,309,922 A | 5/1994 | Schechter et al. | |
| 5,467,775 A | 11/1995 | Callahan et al. | |
| 5,662,105 A | 9/1997 | Tien | |
| 5,680,868 A | 10/1997 | Kahn et al. | |
| 5,853,005 A | 12/1998 | Scanlon | |
| 5,873,836 A | * 2/1999 | Kahn et al. | 600/493 |
| 6,179,783 B1 | 1/2001 | Mohler | |
| 6,520,918 B1 | * 2/2003 | Stergiopoulos et al. | 600/490 |

* cited by examiner

METHOD AND DEVICE FOR MEASURING SYSTOLIC AND DIASTOLIC BLOOD PRESSURE AND HEART RATE IN AN ENVIRONMENT WITH EXTREME LEVELS OF NOISE AND VIBRATIONS

This is a continuation in part of U.S. patent application Ser. No. 09/718,515 filed on Nov. 24, 2000.

FIELD OF THE INVENTION

This invention relates generally to the field of blood pressure monitoring methods and devices and more particularly to auscultatory blood pressure monitoring methods and devices employing means for removing noise and vibration effects from audible blood flow sounds.

BACKGROUND OF THE INVENTION

The blood pressure in the brachial artery is not constant, but varies with time in relation to the beating of the heart. Following a contraction of the heart to pump blood through the circulatory system, the blood pressure increases to a maximum level known as the systolic blood pressure. The minimum blood pressure between heartbeats is known as the diastolic blood pressure.

The traditional technique for measuring the blood pressure of a patient employs an inflatable pressure cuff wrapped around an upper arm of a patient whose blood pressure is to be determined. As the pressure cuff is inflated, cuff pressure and pressure applied to the arm of the patient increases. If the pressure applied to the arm is increased beyond the highest blood pressure in the brachial artery located in the arm beneath the pressure cuff, the artery will be forced to close.

As the pressure in the inflatable cuff is reduced from a high level above the systolic blood pressure, where the brachial artery is permanently closed, to a level below the systolic blood pressure level, the brachial artery beneath the cuff will begin to open and close with each heart beat as the blood pressure first exceeds the cuff pressure and then falls below the cuff pressure. As the blood pressure exceeds the cuff pressure, the artery will open, and a low frequency blood pressure sound, the so-called "Korotkoff sound" can be detected. This sound is detected using a stethoscope or microphone placed near the down-stream end of the cuff on the patient's arm. The highest cuff pressure at which the Korotkoff sounds are detectable thus corresponds to the systolic blood pressure of the patient.

As the cuff pressure is reduced further, the cuff pressure will be brought below the diastolic blood pressure. At this pressure level, the brachial artery beneath the cuff remains open throughout the heart beat cycle. Blood pressure sounds, caused by the opening of the artery will, therefore, not be produced. The lowest cuff pressure at which the blood pressure sounds can be detected thus corresponds to the diastolic blood pressure of the patient. The determination of blood pressure based on the detection of the onset and disappearance of blood pressure sounds as varying pressures are applied to an artery, is known as auscultatory blood pressure determination.

In manual auscultatory blood pressure measurement methods, a stethoscope is used to detect the onset and disappearance of the blood pressure sounds. Thus, the blood pressure measurement is highly dependent on the skill and hearing ability of the person taking the measurement. To overcome this dependence on human skill and judgement, and to automate the process of determining a patient's blood pressure, automatic blood pressure monitoring systems based on the auscultatory method of blood pressure determination have been developed. These automatic systems employ one or more microphones placed in or under an inflatable cuff to detect blood pressure sounds.

However, it is almost impossible to detect the blood pressure sounds in a noisy environment such as a moving ambulance, helicopter, airplanes, or naval vessels.

Pneumatic systems measuring pressure variations caused by blood flowing through the artery instead of sound are not sensitive to noise, but extremely sensitive to movement and vibrations. Pressure variations caused by patient movement and any vibrations present are generally much larger than the pressure variations by the blood flow thus rendering these systems useless in the environments mentioned above.

Some blood pressure monitoring systems employ two microphones for detecting blood pressure sounds. For example, two microphones may be placed under the inflatable cuff separated by a distance such that a low frequency blood pressure sound will reach the first microphone 180 degrees out of phase from the second microphone. Noise signals will tend to reach each microphone essentially simultaneously, and in phase. Therefore, subtracting the two microphone signals from each other will tend to enhance the useful data and diminish unwanted noise. The two microphone signals can be added and subtracted from each other to create signal and noise detection thresholds. Microphone signals are considered to be valid blood pressure sound detections if they meet the detection thresholds. These blood pressure monitoring methods tend obtain useful data in moderately noisy environments. However, these systems are less effective when confronted with significant noise levels.

In U.S. Pat. No. 5,680,868 issued to Kahn et al. in Oct. 28, 1997 a method and apparatus for monitoring the blood pressure of a patient by detecting low frequency blood pressure sounds in the presence of significant noise levels is disclosed. Kahn discloses two microphones placed over the brachial artery of a patient to detect the onset and disappearance of blood pressure sounds in the artery as the pressure on the artery is varied. The microphones are placed on the patient separated by a distance such that a true blood pressure sound will preferably be picked up at the second microphone approximately 180 degrees out of phase with respect to the blood pressure sound picked up by the first microphone. The shift in phase between the signals from the two microphones is used to indicate the detection of a blood pressure sound in the presence of significant noise levels. However, the phase detection method is still affected by vibrations detected out of phase at the two microphones. This method is based on the assumption that noise and vibrations are detected at both microphones without a phase shift whereas the blood pressure sound has a phase shift of approximately 180 degrees. Vibrations due to body motion such as shivering or ambient vibrations imposed on the body will generally be detected out of phase at the two microphones making it difficult to detect the beginning and end of a blood pressure sound signal as the pressure cuff deflates. Furthermore, this method requires an extensive amount of computation making it difficult to manufacture a portable device using this method. Another disadvantage of this method is that it is not possible to obtain directly from the processed signals a heart rate, which provides live saving information in emergency situations.

It is an object of the invention to provide a method and a device for measuring systolic and diastolic blood pressure in environments comprising extreme levels of noise and vibration, which overcomes the aforementioned problems.

It is further an object of the invention to provide a method and a device for measuring systolic and diastolic blood pressure in environments comprising extreme levels of noise and vibration that also provides information about the heart rate.

It is yet another object of the invention to provide a method and a device for measuring systolic and diastolic blood pressure in environments comprising extreme levels of noise and vibration enabling accurate measurement of blood pressure during low flow states, such as cardiogenic shock.

It is yet another object of the invention to provide a device for measuring blood pressure in environments comprising extreme levels of noise and vibration that is battery operated and portable.

SUMMARY OF THE INVENTION

In accordance with the present invention there is provided, a method and device for measuring systolic and diastolic blood pressure and heart rate in environments with extreme levels of noise and vibrations. Sensing noise and vibrations and subtracting it from a measured blood pressure signal using an adaptive interferer canceller provides good results even under extreme conditions such as aboard a helicopter.

In accordance with the present invention there is provided, a method for measuring systolic and diastolic blood pressure of a patient comprising the steps of:

sensing blood pressure signals corresponding to Korotkoff sound using a first acoustic sensor placed on the patient near a location of an artery of the patient, the first acoustic sensor for producing a first acoustic signal in dependence upon the blood pressure signals;

sensing noise and vibrations using a second acoustic sensor for producing a second acoustic signal in dependence upon noise and vibrations, the second sensor being placed on the patient at a location away from an artery such that the second acoustic signal enables reliable signal processing for measuring systolic and diastolic blood pressure using adaptive interference cancellation;

sensing pressure applied to the artery using a pressure transducer for sensing pressure and for providing a pressure signal in dependence upon the sensed pressure;

providing the first acoustic signal, the second acoustic signal and the pressure signal to a processor while the pressure is applied to the artery;

processing the first acoustic signal for removing interference due to noise and vibrations in the first acoustic signal by subtracting the second acoustic signal from the first acoustic signal using the adaptive interference cancellation;

detecting Korotkoff sound pulses within the processed first acoustic signal; and, determining systolic and diastolic pressure by relating the detected Korotkoff sound pulses to the pressure signal.

In accordance with the present invention there is further provided, a method for monitoring heart beat of a patient within a noisy environment comprising the steps of:

sensing blood pressure signals corresponding to heart beat using a first acoustic sensor (or array of sensors) placed on the patient near a location of an artery of the patient, the first acoustic sensor for producing a first acoustic signal in dependence upon the blood pressure signals;

sensing noise and vibrations using a second acoustic sensor for producing a second acoustic signal in dependence upon noise and vibrations, the second sensor being placed on the patient at a location away from an artery such that the second acoustic signal enables reliable signal processing for measuring systolic and diastolic blood pressure using adaptive interference cancellation;

providing the first acoustic signal and the second acoustic signal to a processor;

removing interference due to noise and vibrations in the first acoustic signal by subtracting the second acoustic signal from the first acoustic signal using the adaptive interference cancellation techniques;

detecting Korotkoff sound pulses within the first acoustic signal; and, determining a heart rate from the detected Korotkoff sound pulses.

In accordance with the present invention there is further provided, a device for measuring systolic and diastolic blood pressure of a patient in an environment with extreme levels of noise and vibration, the device comprising:

a pressure cuff for applying pressure to an artery of the patient;

a pressure transducer for providing a pressure signal in dependence upon the pressure applied to the artery;

a first acoustic sensor for producing a first acoustic signal in dependence upon blood pressure signals corresponding to Korotkoff sounds;

a second acoustic sensor for producing a second acoustic signal in dependence upon noise and vibration, the second sensor being placed such that the second acoustic signal enables reliable signal processing for measuring systolic and diastolic blood pressure using adaptive interference cancellation; and, a processor for processing the first acoustic signal using the second acoustic signal using the adaptive interference cancellation, for detecting Korotkoff sound pulses within the processed first acoustic signal and for determining systolic and diastolic blood pressure using the detected Korotkoff sound pulses and the pressure signal.

In accordance with the present invention there is further provided, a method for measuring systolic and diastolic blood pressure of a patient comprising the steps of:

applying pressure to a brachial artery of the patient by wrapping a pressure cuff around a limb of the patient, the pressure cuff having a first surface being in contact with the skin of the patient's limb and a second surface opposite the first surface facing away from the skin of the patient's limb;

sensing blood pressure signals corresponding to Korotkoff sound using a first acoustic sensor placed on the patient's skin over the brachial artery of the patient, the first acoustic sensor for producing a first acoustic signal in dependence upon the blood pressure signals;

sensing noise and vibrations using a second acoustic sensor for producing a second acoustic signal in dependence upon noise and vibrations, the second sensor being attached to the second surface and acoustically isolated therefrom;

sensing pressure applied to the artery using a pressure transducer for sensing pressure and for providing a pressure signal in dependence upon the sensed pressure;

providing the first acoustic signal, the second acoustic signal and the pressure signal to a processor while the pressure is applied to the artery;

processing the first acoustic signal for removing interference due to noise and vibrations using the second acoustic signal in an adaptive interferer canceller;

detecting Korotkoff sound pulses within the processed first acoustic signal; and, determining systolic and diastolic pressure by relating the detected Korotkoff sound pulses to the pressure signal.

In accordance with the present invention there is further provided, a device for measuring systolic and diastolic blood pressure of a patient in an environment with extreme levels of noise and vibration, the device comprising:

a pressure cuff for being wrapped around a limb of the patient for applying pressure to the brachial artery of the patient, the pressure cuff having a first surface for being in contact with the skin of the patient's limb and a second surface opposite the first surface for facing away from the skin of the patient's limb;

a pressure transducer for providing a pressure signal in dependence upon the pressure applied to the brachial artery;

a first acoustic sensor for placement on the patient's skin over a brachial artery for producing a first acoustic signal in dependence upon blood pressure signals corresponding to Korotkoff sounds;

a second acoustic sensor attached to the second surface and acoustically isolated therefrom for producing a second acoustic signal in dependence upon noise and vibration; and, a processor for processing the first acoustic signal and the second acoustic signal using adaptive interference cancellation, for detecting Korotkoff sound pulses within the processed first acoustic signal and for determining systolic and diastolic blood pressure using the detected Korotkoff sound pulses and the pressure signal.

In accordance with an aspect of the present invention there is provided, a device for measuring systolic and diastolic blood pressure of a patient in an environment with extreme levels of noise and vibration, the device comprising:

a pressure cuff for being wrapped around a limb of the patient for applying pressure to the brachial artery of the patient, the pressure cuff having a first surface for being in contact with the skin of the patient's limb and a second surface opposite the first surface for facing away from the skin of the patient's limb;

a pressure transducer for providing a pressure signal in dependence upon the pressure applied to the brachial artery;

a first acoustic sensor attached to the first surface for placement on the patient's skin over a brachial artery at the downstream end of the pressure cuff with respect to the blood flow in the brachial artery for producing a first acoustic signal in dependence upon blood pressure signals corresponding to Korotkoff sounds;

a second acoustic sensor attached to the second surface and acoustically isolated therefrom for producing a second acoustic signal in dependence upon noise and vibration, the second acoustic sensor being attached approximately opposite to the location of the first acoustic sensor with respect to the patient's limb at the upstream end of the pressure cuff; and, a processor for processing the first acoustic signal and the second acoustic signal using adaptive interference cancellation, for detecting Korotkoff sound pulses within the processed first acoustic signal and for determining systolic and diastolic blood pressure using the detected Korotkoff sound pulses and the pressure signal.

BRIEF DESCRIPTION OF THE DRAWINGS

Exemplary embodiments of the invention will now be described in conjunction with the following drawings, in which:

FIG. 6a illustrates a processed Korotkoff sound signal for a patient with arrhythmia; and, FIG. 6b illustrates a pressure deflation curve corresponding to the Korotkoff sound signal illustrated in FIG. 6a.

DETAILED DESCRIPTION

Figure 1A:
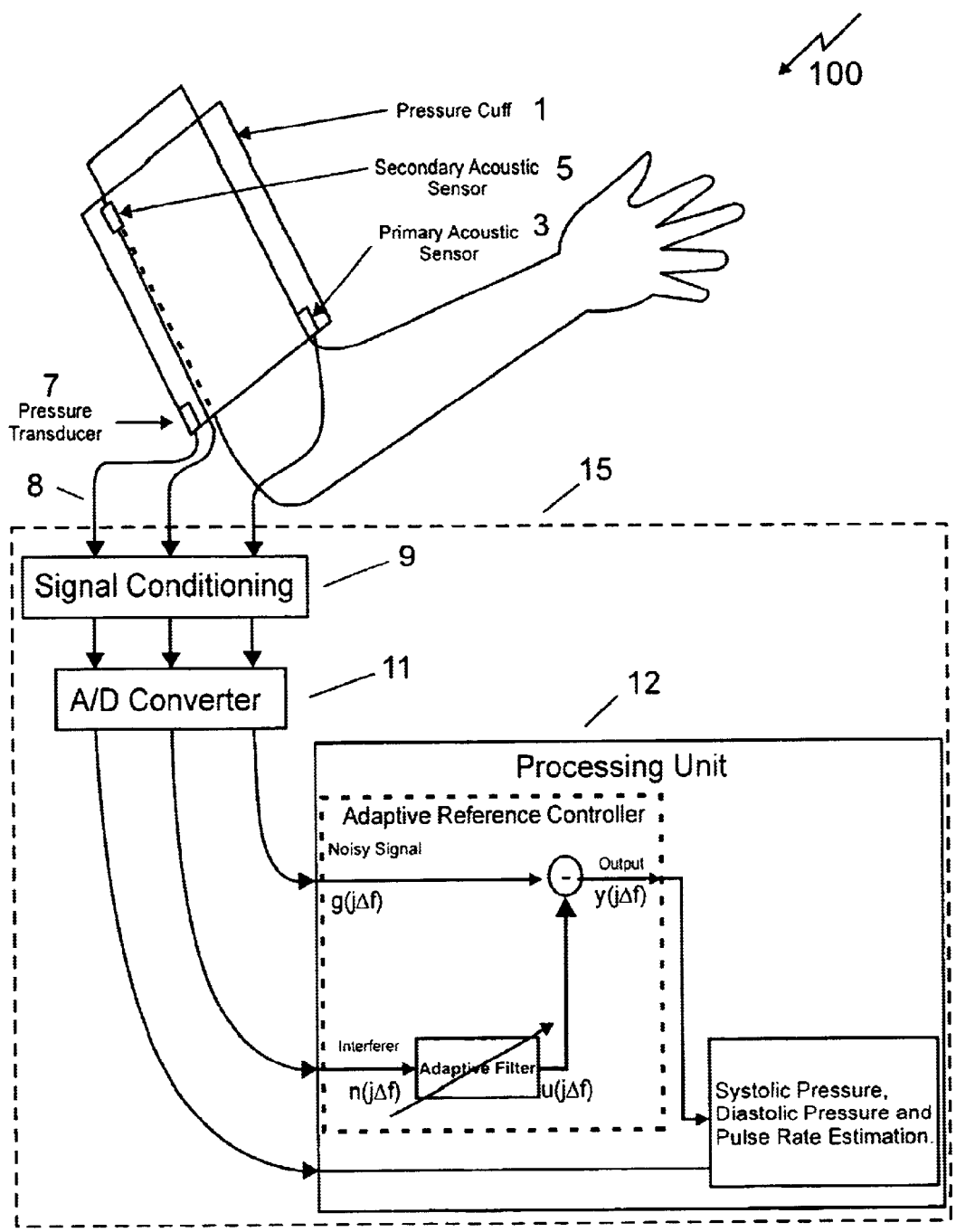
FIG. 1a is a simplified diagram of a device for measuring systolic and diastolic blood pressure in environments comprising extreme levels of noise and vibration according to the invention.

FIG. 1a illustrates schematically a device 100 for measuring systolic and diastolic blood pressure—sphygmomanometer—in environments comprising high levels of noise and vibration according to the invention. The device 100 comprises a pressure cuff 1 to be wrapped around a limb of a patient whose blood pressure is to be determined. When wrapped around the patient's limb the pressure cuff 1 substantially forms a cylinder 17-07 US CIP Patent having an inside surface 22 and an outside surface 24. Within the pressure cuff 1 is mounted a primary acoustic sensor 3, a secondary acoustic sensor 5 and a pressure transducer 7. The primary acoustic sensor 3 captures blood pressure sounds and provides an electromagnetic blood pressure signal in dependence thereupon. The secondary acoustic sensor 5 captures ambient noise and vibrations and provides an electromagnetic signal in dependence thereupon. The pressure transducer 7 measures cuff pressure, i.e. pressure exerted by the inflated pressure cuff 1 onto a brachial artery of the patient. The primary acoustic sensor 3 is located on the inside 22 of the pressure cuff 1 for positioning on the skin of the patients limb over the brachial artery at the downstream end of the pressure cuff 1 with respect to blood flow in the brachial artery. The secondary acoustic transducer 5 is located away from the brachial artery in order to capture noise and vibrations superposed to the blood pressure sound signal detected by the primary acoustic sensor 3. The pressure cuff 1 is connected via a communication link 8 to a housing 15 comprising means for signal conditioning 9 such as filtering, an A/D converter 11 and a processor 12.

In operation the pressure cuff 1 wrapped around an upper arm of the patient is inflated to a pressure beyond the highest blood pressure in the brachial artery forcing the artery to close. The pressure cuff 1 is inflated manually or by a motor driven pump.

Figure 1B:
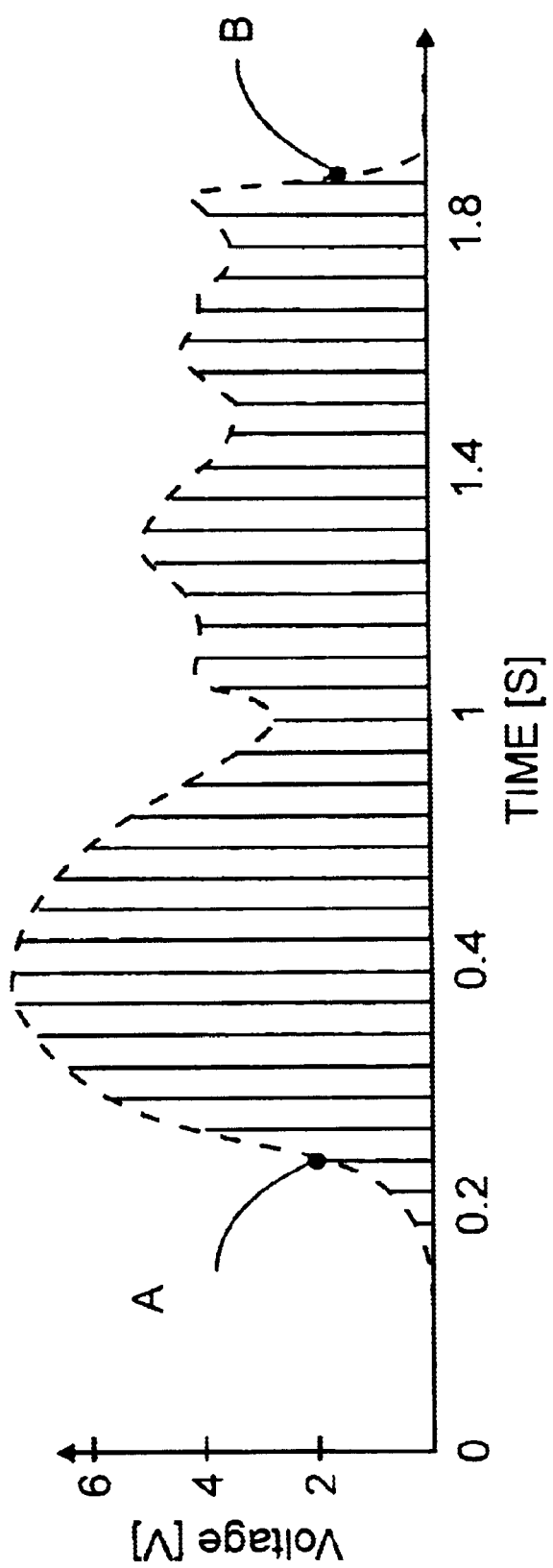
FIG. 1b illustrates schematically a processed Korotkoff sound signal and its envelope for determining systolic and diastolic blood pressure.

As the pressure in the inflatable cuff is reduced to a level below the systolic blood pressure level, the brachial artery beneath the cuff will begin to open and close with each heart beat as the blood pressure first exceeds the cuff pressure and then falls below the cuff pressure. The arterial wall acts in a non-linear fashion with respect to the blood pressure level. Thus, as the blood pressure exceeds the cuff pressure, the artery will open, producing a low frequency blood pressure sound corresponding to the heart beat. This sound is then detected using the primary acoustic sensor 3. Therefore, the pressure detected by the pressure transducer 7 at the time instance when a first blood pressure sound is detected is the systolic blood pressure. More specifically, the systolic pressure is defined as the occurrence of the point of greatest magnitude of the positive derivative of the processed signals envelope—surrounding the detected Korotkoff sounds—as indicated by the dashed curve in FIG. 1b. This processing step is synonymous with the blood pressure when the first Korotkoff is heard, at the marked increase A in the envelope shown in FIG. 1b.

As the cuff pressure is reduced further, the cuff pressure will be brought below the diastolic blood pressure. At this pressure level, the brachial artery beneath the cuff remains open throughout the heart beat cycle. Blood pressure sounds, caused by the opening of the artery will, therefore, not be produced. The lowest cuff pressure at which the blood pressure sounds are detected thus corresponds to the diastolic blood pressure. This marked decrease B is the point of greatest negative slope of the envelope surrounding the Korotkoff sounds, as indicated by the dashed curve in FIG. 1b.

During deflation of the pressure cuff 1 ambient noise and vibrations are detected using the secondary acoustic sensor 5. Sensor signals produced by the acoustic sensors 3 and 5 and the pressure transducer 7 are transmitted via the communication link 8 to the processor 12 for processing.

Figure 2:
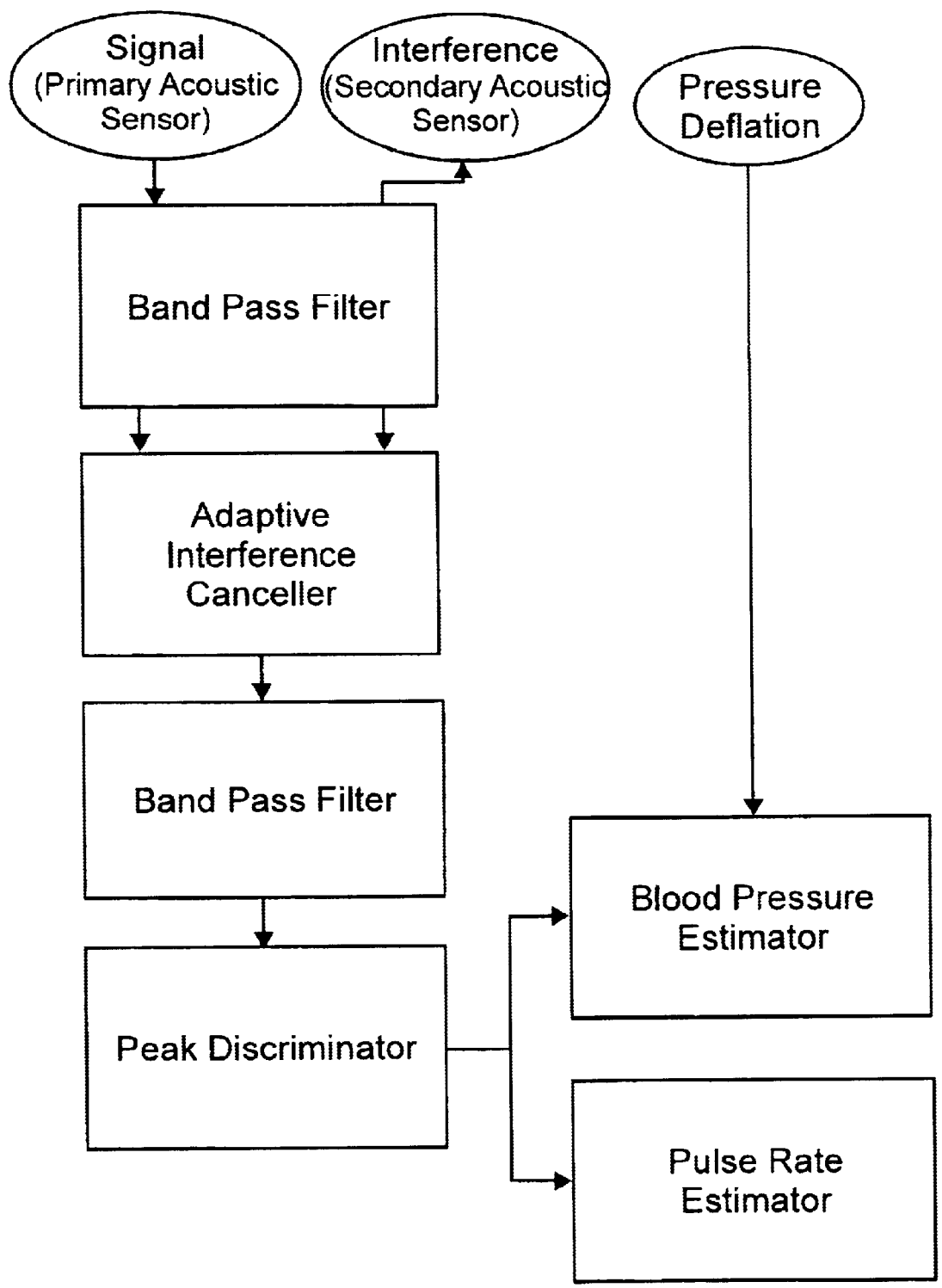
FIG. 2 is a simplified diagram of a signal processing structure according to the invention.

The signals are then processed according to the invention as shown in FIG. 2. In a first optional step the sensor signals are processed in signal conditioning means 9 such as a band pass filter. Since the frequency range of the acoustic signal of interest is well localized using a band pass filter is a useful step for removing excess noise outside this frequency range of interest. The filtered signals are then converted into corresponding digital signals using an A/D converter 11 for provision to the processor 12 such as a microprocessor. In the processor 12 the acoustic sensor signals are then processed using an adaptive interferer canceller, indicated in FIG. 1a by dotted lines, in order to remove any interference n(jΔt)—detected by the secondary acoustic sensor 5—from the noisy measured signal s(jΔt)—detected by the primary acoustic sensor 3. The noisy measured signal s(jΔt) is provided to the adaptive interferer canceller as input signal. The signal n(jΔt) provided by the secondary acoustic sensor 5 is provided to an adaptive filter of the adaptive interferer canceller as an interference noise signal. The output of the adaptive filter u(jΔt) for the interferer input n(jΔt) is given by equation (1):

$$u(j\Delta t) = \sum_{i=1}^{L} w_i^{j\Delta t} \times n\left(\left(j+i-\frac{L}{2}\right)\Delta t\right), (i=1, 2, \ldots L), (j=1, 2, \ldots K), \quad (1)$$

wherein L is the number of adaptive weights ($w_1, w_2 \ldots w_L$) at time jΔt and K is the maximum number of samples to be processed. The adaptive weights for the adaptive weight algorithm (1) are given by the adaptive weight update equations (2):

$$w_i^{(j+1)\Delta t} = w_i^{j\Delta t} + \left(\frac{\lambda}{a+|n|}\right) \times n\left(\left(j+i-\frac{L}{2}\right)\Delta t\right) \times y(j\Delta t), \quad (2)$$

$$(i=1, 2, \ldots L), (j=1, 2, \ldots K),$$

wherein λ is an adaptive step size parameter, a is a stability parameter and |n| is the Euclidean norm of the vector:

$$\left[n\left(\left(j+1-\frac{L}{2}\right)\Delta t\right), n\left(\left(j+2-\frac{L}{2}\right)\Delta t\right), \ldots n\left(\left(j+\frac{L}{2}\right)\Delta t\right)\right].$$

The output of the adaptive interferer canceller is then given by y(jΔt)=s(jΔt)−u(jΔt). In order to calculate the adaptive weight for a sample (j+1)Δt to be processed the output of the interferer canceller of the previous sample jΔt is used as can be seen in the adaptive weight update equation (2).

This algorithm is an ideal tool for removing any noise and vibration effects in a measured signal if an interferer is accurately measured. The noise measured by the second acoustic sensor 5 placed away from the brachial artery is treated as the interferer n(jΔt) and an adaptive weighted signal u(jΔt) is then subtracted from the measured acoustic signal of the blood pressure sound s(jΔt). Detailed information concerning the adaptive interferer canceller are disclosed by the inventor in "Implementation of Adaptive and Synthetic-Aperture Processing Schemes in Integrated Active-Passive Sonar Systems", published in Proceedings of the IEEE, 86(2), 358–396, February 1998.

The adaptive interferer canceller has been found to be a powerful tool for removing interference noise from a "noisy" signal if the interference is accurately measured. Furthermore, the adaptive interferer canceller as applied in the device and method for measuring blood pressure according to the invention requires only a minimum amount of computation in order to provide good results even for signals detected in environments with extreme noise and vibration levels.

Optionally, to further reduce noise effects the output signal y(jΔt) may be band pass filtered.

The output signal y(jΔt) is then provided to a peak discriminator in order to extract valid peaks resulting from heartbeats in the acoustic signal y(jΔt) from any background noise. In a first step peaks greater than a noise floor level determined by the peak discriminator are isolated. The isolated peaks are then further examined in order to determine if they satisfy periodicity and constancy in repetition, that is beats are not missing, as is expected from heartbeats. Peaks not satisfying these constraints are discarded. The output of the peak discriminator is a series of constantly repeating periodic peaks. This process also eliminates random peaks due to strong transient noise effects. As is obvious to a person of skill in the art, there are numerous methods for detecting peaks. The method described above has been found to produce good results even in environments with extreme high noise and vibration levels while the required computation is kept to a minimum.

From the results of the peak discriminator a pulse rate estimator determines the immediately available pulse rate of the patient.

The output of the peak discriminator is also provided to a blood pressure estimator. The systolic blood pressure is defined as the blood pressure when the first heartbeat is detected as the pressure cuff 1 is deflating. The diastolic blood pressure is defined as the blood pressure when the last heartbeat is detected. From the results of the peak discriminator the time instances where these two pulse peaks occur are determined and then used as a reference to the signal acquired by the pressure transducer 7. The signal acquired by the pressure transducer 7 provides a measurement of the pressure in the deflating pressure cuff 1 as a function of time. The corresponding pressures at these time instances are the systolic blood pressure and the diastolic blood pressure, respectively.

Alternatively, the measurements are taken while the pressure cuff 1 is being inflated. This method has the advantage that the pressure cuff 1 is inflated to a pressure only slightly above the systolic blood pressure whereas in the above method the pressure cuff is inflated to a pressure much higher than the actual systolic blood pressure in order to ensure closure of the brachial artery.

Furthermore, a plurality of acoustic sensors, or array of sensors, may be used for each of detecting blood pressure signals and interference noise in order to further improve signal quality.

Figure 3:
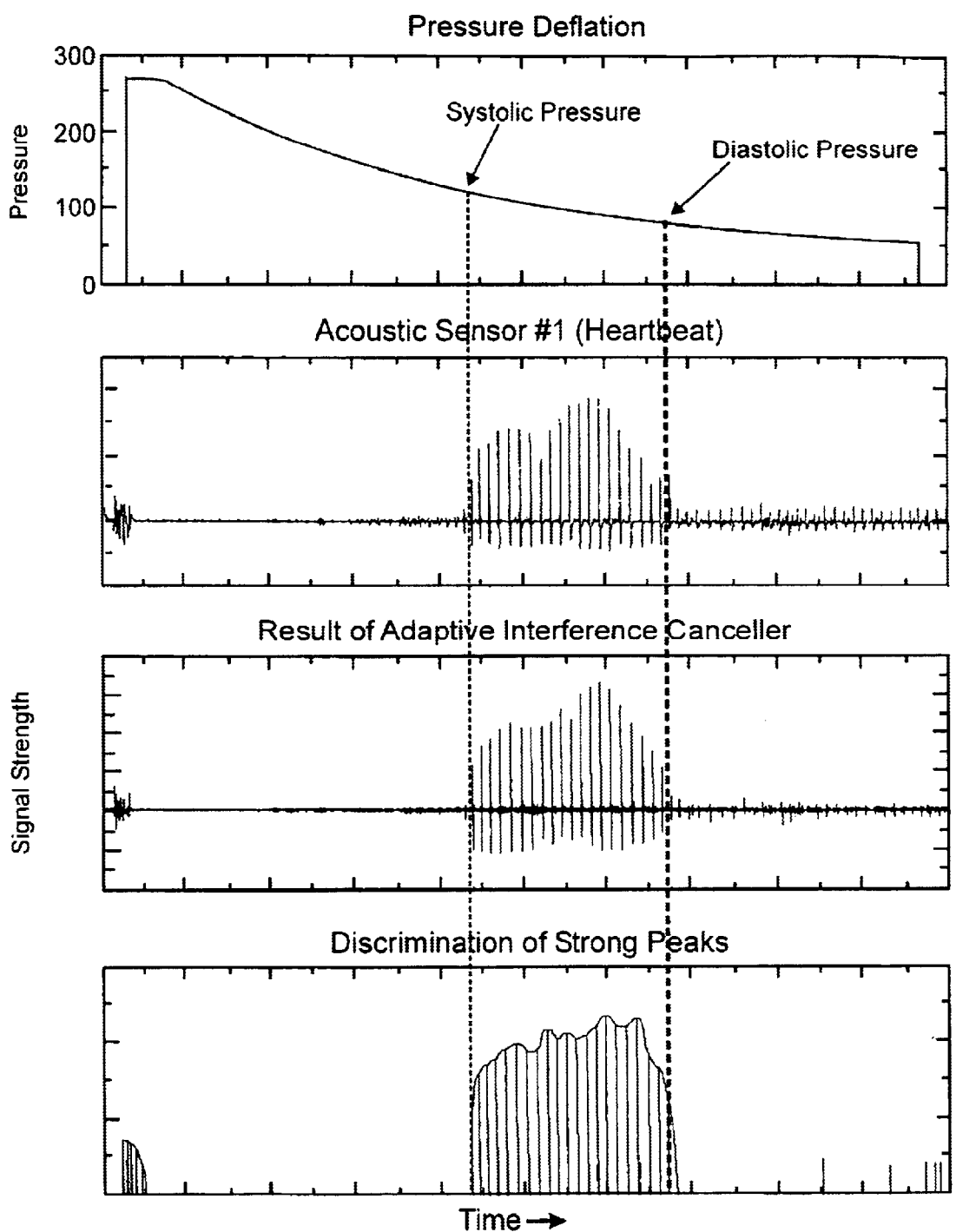
FIG. 3 illustrates results of the signal processing according the invention of real signals captured in a relatively noiseless environment.

FIG. 3 shows results of the device and method for measuring blood pressure and heart rate according to the invention in an almost noiseless environment. The top curve indicates pressure deflation of the pressure cuff 1 as function of time. The second curve from top shows the acoustic signal measured by the primary acoustic sensor 3. Periodic pulses resulting from the Korotkoff sound are clearly visible and the first and last pulse are well defined. The next curve shows the acoustic signal after it has been processed by the adaptive interferer canceller. It is evident that the noise level is lower in this signal and residual Korotkoff sounds present in the unprocessed signal have been removed. The bottom curve shows the peaks discriminated by the peak discriminator from the noise. Small areas at the beginning and the end are discarded due to their non-periodic nature and the fact that they are not constant over a period that could be deemed to be a series of heart beats. The remaining sequence is retained and used to determine blood pressure and heart rate. In this case the systolic blood pressure is 123 psi, the diastolic blood pressure is 83 psi and the heart rate is 84 beats per minute.

Figure 4:
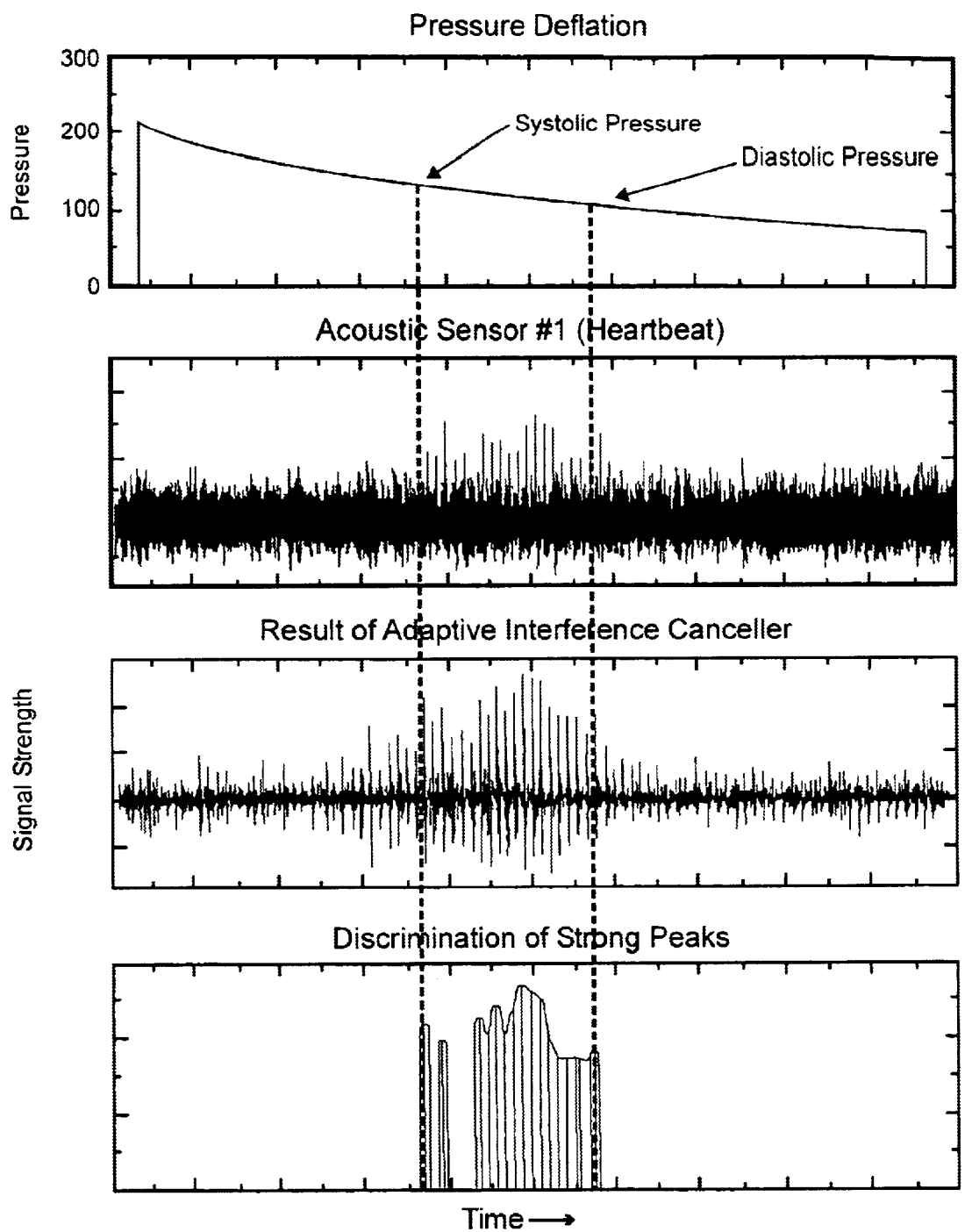
FIG. 4 illustrates results of the signal processing according the invention of real signals captured in presence of intense noise and vibrations.

FIG. 4 shows results for measurements taken aboard a helicopter—an environment comprising extreme noise and vibration levels. It is evident that the signal detected by the primary acoustic sensor is very noisy and the first and the last pulse cannot directly be identified. However, after processing the signal using the adaptive interferer canceller and the first stage of the peak discrimination the first and the last pulse are readily identified. The systolic and diastolic blood pressures are 132 psi and 108 psi, respectively, and the heart rate is 92 beats per minute. These measurements, as well as those taken under noiseless conditions compare favorably with measurements taken by the traditional auscultatory method by a medical practitioner immediately before the experiments using the device according to the invention.

The device and method for measuring the blood pressure and heart rate according to the invention is highly advantageous to the prior art by providing good results in environments with extreme levels of noise and vibration. In many emergency situations it is essential for saving the live of a victim to obtain accurate measurements of blood pressure and heart rate in order to provide first emergency treatment. Unfortunately, in many cases this has to be done in a very noisy environment such as an ambulance, a helicopter or a naval vessel. This invention provides the means to obtain accurate results under such conditions and allows measurements of blood pressure and heart rate even if the victim is under cardiogenic shock. The signal processing requires only a minimum of computation, therefore, the device for measuring blood pressure and heart rate may be battery operated and assembled in a small portable housing. For example, such a device allows measurement of the blood pressure while the victim is transported on a stretcher to an ambulance, thus saving valuable time.

In another embodiment the device according to the invention is used to monitor the heart rate during transportation. In this case the pressure cuff 1 is inflated only slightly above the diastolic pressure in order to be able to detect the Korotkoff sound but not to interrupt the blood flow through the artery.

For the implementation of the adaptive interferer canceller it is critical to strategically place the two sensors, the primary acoustic sensor 3 for producing a first acoustic signal in dependence upon the blood pressure signals—Korotkoff sounds—and the secondary acoustic sensor 5 for producing a second acoustic signal in dependence upon noise and vibrations. The secondary acoustic sensor 5 is placed such that the phase characteristics and properties of the interference signal are substantially identical to the phase characteristics and properties of the interference signal sensed by the primary acoustic sensor 3. Furthermore, if there is a correlation coupling term for the signal of interest between the two acoustic sensors the adaptive interference cancellation process will remove the signal of interest. Therefore, the secondary acoustic sensor 5 is placed at a location where it is unlikely that components of the signal of interest—Korotkoff sounds—are sensed by the secondary acoustic sensor 5.

The following description of the signal processing using adaptive interference cancellation disclosed by B. Widrow and S. Stearns "Adaptive Signal Processing", Prentice Hall, Englewood Cliffs, N.J. 07632, 1985 illustrates the need for strategically placing the secondary acoustic sensor 5.

The first acoustic signal is defined by $y(j\Delta t)=s(j\Delta t)+n(j\Delta t)$, where $s(j\Delta t)$ and $n(j\Delta t)$ are signal and noise components, respectively. In the adaptive interference cancellation process with performance feedback it is essential that the noise component is sensed simultaneously with the received noisy signal. Assume that the noise measurements provided by the secondary acoustic sensor 5 to the input of the adaptation process shown in FIG. 1a are defined by the input vector $\bar{\epsilon}$ with terms $[\epsilon(\Delta t), \epsilon(2\Delta t), \ldots, \epsilon(M\Delta t)]^T$, wherein M is the maximum number of samples to be processed. Furthermore, the output of a least mean square adaptation process is a linear combination of the input measurements $\bar{\epsilon}$ and the weight coefficients $[w(\Delta t), w(2\Delta t), \ldots, w(M\Delta t)]^T$ of the vector $\bar{W}$ that are derived by descending toward the minimum of the surface of the performance feedback. The output of the adaptive interferer canceller is then given by:

$$e = \bar{Y} - \bar{\epsilon}^T \bar{W} \qquad (3)$$

where, $\bar{Y}$ is the input vector of the noisy measurements from the first acoustic sensor, $y(j\Delta t)$ for $j=1,2,\ldots,M$. The adaptive interference cancellation process is based on the minimization of the square of equation (3), $E_{min}[(\bar{e})^2]=E_{min}[(\bar{S}+\bar{N})^2]-E_{min}[(\bar{\epsilon}^T W)^2]$. From this results that when $E[\bar{e}]$ is minimized then the signal power $E[\bar{S}]$ is unaffected and the term $E[(\bar{N}-\bar{\epsilon}^T W)^2]$ is minimized. Therefore, the output of the adaptive interference cancellation process provides estimates of the signal vector, i.e. $E_{min}[\bar{e}]=E[\bar{S}]$.

However, if the second sensor senses components of the noise $\bar{\epsilon}$ and the signal $\bar{S}$, then the adaptive interference cancellation process will cancel the signal of interest and the output of the adaptive interference cancellation process will be white noise $E_{min}[\bar{e}]=E[\bar{e}]$.

Figure 5A:
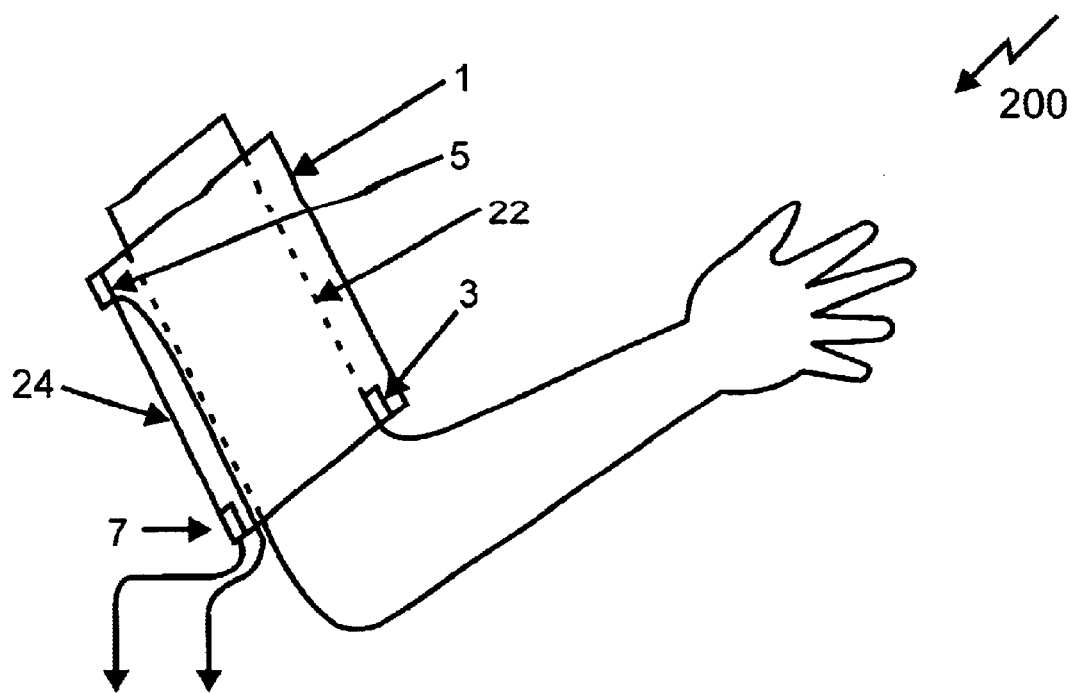
FIG. 5a is a simplified diagram of a pressure cuff illustrating the positioning of acoustic sensors of the device for measuring systolic and diastolic blood pressure in environments comprising extreme levels of noise and vibration according to the invention.
Figure 5B:
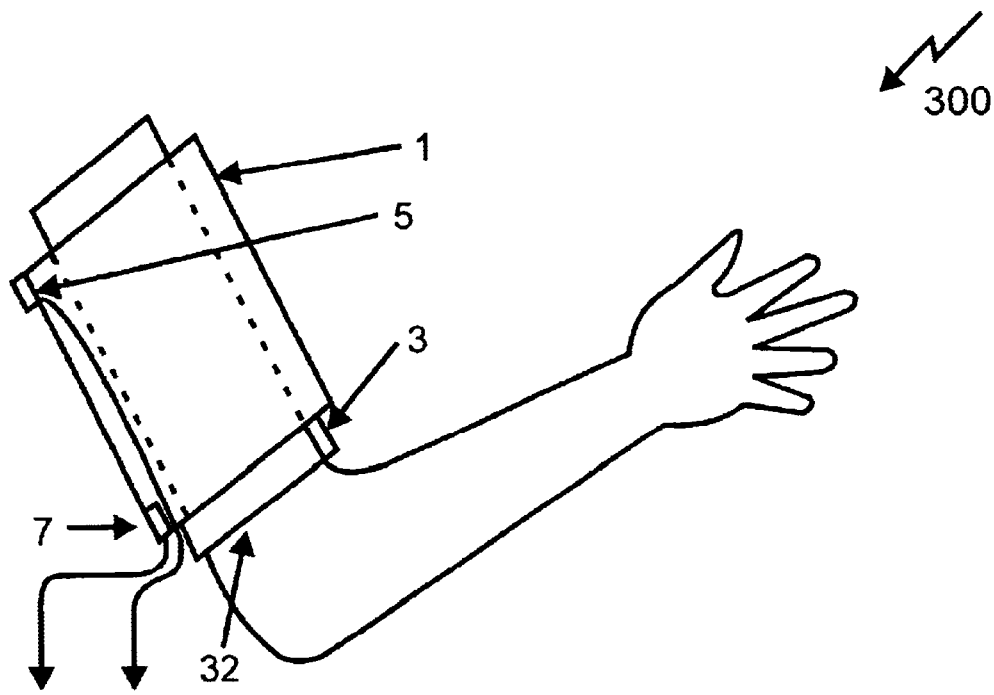
FIG. 5b is a simplified diagram of a pressure cuff illustrating the positioning of acoustic sensors of the device for measuring systolic and diastolic blood pressure in environments comprising extreme levels of noise and vibration according to the invention.

Referring to FIGS. 5a and 5b a detailed view of two embodiments of the device for measuring systolic and diastolic blood pressure according to the invention are shown illustrating the positioning of the acoustic sensors. During clinical trials it has been found that some signal cancellation occurred when the secondary acoustic sensor 5 was in contact with the skin of a patient's limb or housed on inside surface 22 of the pressure cuff 1. In order to overcome the signal cancellation the secondary sensor 5 is placed on outside surface 24 of the pressure cuff 1 as shown in embodiments 200 and 300. Clinical trials have been performed to determine the positions for mounting the secondary acoustic sensor 5 on the pressure cuff 1 such that the second acoustic signal satisfies the above conditions.

During the clinical trials a best position for mounting the secondary acoustic sensor 5 on the pressure cuff 1 has been found to be the position shown in embodiments 200 and 300. As illustrated in embodiment 200 the primary acoustic sensor 3 is placed on the skin of a patient's limb over the brachial artery on the inside surface 22 of the pressure cuff 1 at the downstream end of the pressure cuff 1 with respect to the blood flow in the brachial artery. Alternatively, an array of primary acoustic sensors 3 is placed on the skin of a patient's limb across the brachial artery to ensure detection of the Korotkoff sounds. The secondary acoustic sensor 5 is placed on the outside surface 24 of the pressure cuff 1 at a location approximately diametrically opposite the location of the primary acoustic sensor 3 and at the upstream end of the pressure cuff 1.

Furthermore, the Korotkoff sounds are modulated with the deflated pressure of the pressure cuff 1. If the secondary acoustic sensor 5 has acoustic contact with the pressure cuff 1 the secondary acoustic sensor 5 mounted on the outside of the pressure cuff 1 senses the Korotkoff sounds, resulting in a cancellation of the signal of interest. Therefore, the secondary acoustic sensor 5 is mounted to the pressure cuff 1 in an acoustically isolating fashion. This is accomplished, for example, by housing the acoustic sensor in a thin bell using an elastomer isolator. The acoustic sensors housed in the bell are then attached to pressure cuff 1, the primary acoustic sensor 3 on the inside and the secondary acoustic sensor on the outside. Optionally, the acoustic sensors are removable attached using, for example, hook and loop fasteners for optimal placement of the same by a health care practitioner. This allows the health care practitioner to ensure that the primary acoustic sensor 3 is placed directly over the brachial artery while the secondary acoustic sensor 5 is placed approximately diametrically opposite. Further optionally, an array of, for example, three primary acoustic sensors 3 are housed in the bell to ensure detection of the Korotkoff sounds.

Figure 6A:
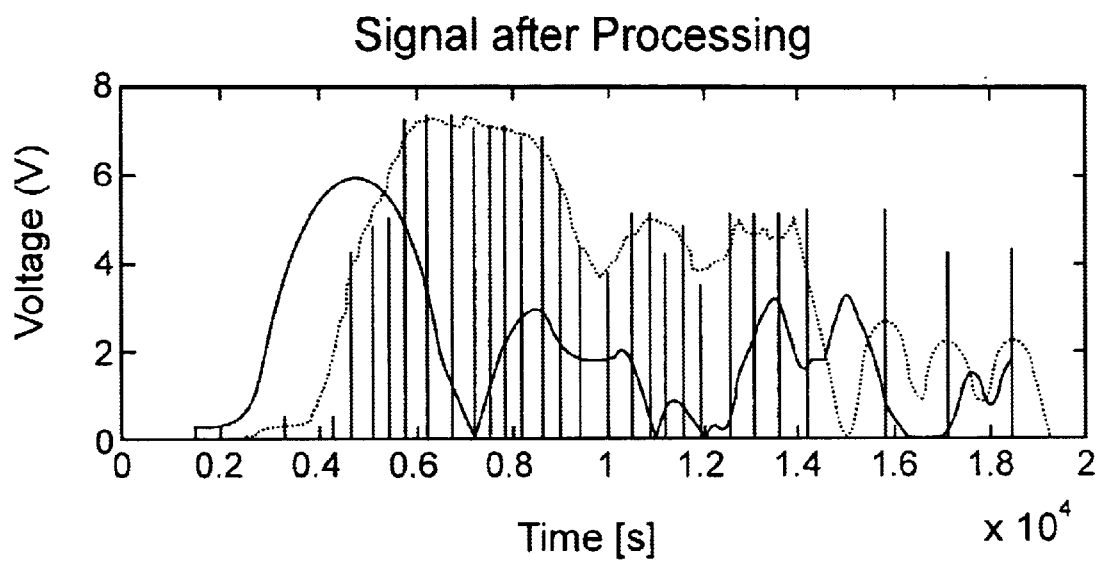
Figure 6B:
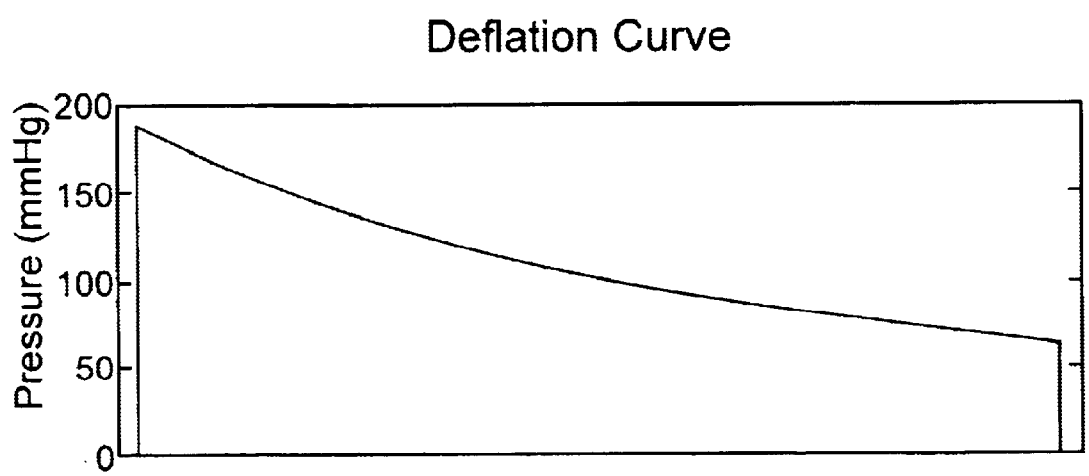

FIGS. 6a and 6b illustrate a processed signal and a corresponding pressure deflation curve for a patient with arrhythmia. Arrhythmia is an alteration in rhythm of the heart beat that causes Korotkoff sound pulses to disappear within the pressure deflation curve. During the peak discrimination process according to the invention the heart rate estimate is updated with each pulse found during searching for the systolic and diastolic pressure. Furthermore, the process keeps track of the number of "missed" heartbeats and determines a new value for the systolic and diastolic pressures if it finds a new sequence of heartbeats after the gap, as shown in FIG. 6a. It is noted that the peak discrimination process according to the invention is highly advantageous since most commercially available systems fail to estimate systolic and diastolic blood pressure for patients with arrhythmia.

In one embodiment of the blood pressure measurement system according to the invention the systolic and diastolic blood pressures are determined based on an electronic equivalent of the corresponding medical definitions of systolic and diastolic pressures, i.e. systolic pressure occurring at the onset of a train of pulses perceptible to the acoustic sensors and diastolic pressure when these pulses disappeared completely. This results in a bias between measurements taken with the system according to the invention using the above signal processing and measurements taken using the conventional auscultatory method. Therefore, in another embodiment of the signal processing according to the invention the above definitions of the systolic and diastolic pressures are specified as the appearance and disappearance of a train of auditory pulses perceptible to an average human ear.

During the clinical trials systolic and diastolic pressure measured using the blood pressure measurement system according to the invention were repeatedly lower than systolic and diastolic pressure measured using the conventional auscultatory method. Furthermore, the difference was larger for the systolic pressure than the diastolic pressure. The consistent difference in blood pressure measurements resulted from the positioning of the bell housing the primary acoustic sensor 3 underneath the inflated pressure cuff exerting additional pressure on the artery. This effect is more apparent at higher pressures, affecting the systolic pressure to a greater degree than the diastolic pressure. To overcome this difference in the measurements taken using the system according to the invention and the conventional auscultatory method the bell housing of the primary sensor 3 has a surface area for contacting a patients skin that is large enough to substantially reduce the additional pressure exerted on the artery. Alternatively, the bell housing of the primary sensor 3 is attached to a non inflatable extension 32 of the pressure cuff 1 as illustrated in embodiment 300.

Of course, numerous other embodiments may be envisaged without departing from the spirit and scope of the invention.

What is claimed is:

1. A method for measuring systolic and diastolic blood pressure of a patient comprising the steps of:

applying pressure to a brachial artery of the patient by wrapping a pressure cuff around a limb of the patient, the pressure cuff having a first surface being in contact with skin of the patient's limb and a second surface opposite the first surface facing away from the skin of the patient's limb;

sensing blood pressure signals corresponding to Korotkoff sounds using a first acoustic sensor placed on the skin of the patient's limb over the brachial artery, the first acoustic sensor for producing a first acoustic signal in dependence upon the blood pressure signals;

sensing noise and vibrations using a second acoustic sensor for producing a second acoustic signal in dependence upon noise and vibrations, the second sensor being attached to the second surface and acoustically isolated therefrom;

sensing the pressure applied to the brachial artery using a pressure transducer for sensing pressure and for providing a pressure signal in dependence upon the sensed pressure;

providing the first acoustic signal, the second acoustic signal and the pressure signal to a processor while the pressure is applied to the brachial artery;

processing the first acoustic signal for removing interference due to noise and vibrations using the second acoustic signal in an adaptive interferer canceller;

detecting Korotkoff sound pulses within the processed first acoustic signal; and, determining systolic and diastolic pressure by relating the detected Korotkoff sound pulses to the pressure signal.

2. A method for measuring systolic and diastolic blood pressure of a patient as defined in claim 1, wherein the pressure is applied to the brachial artery such that the brachial artery is forced closed.

3. A method for measuring systolic and diastolic blood pressure of a patient as defined in claim 2, comprising the step of reducing the pressure applied to the brachial artery.

4. A method for measuring systolic and diastolic blood pressure of a patient as defined in claim 2, wherein the blood pressure signals are sensed while performing the step of applying pressure to the brachial artery until the brachial artery is forced closed.

5. A method for measuring systolic and diastolic blood pressure of a patient as defined in claim 2, wherein the first acoustic sensor is placed on the skin of the patient's limb over the brachial artery of the patient downstream of a location where the pressure is applied to the brachial artery.

6. A method for measuring systolic and diastolic blood pressure of a patient as defined in claim 5, wherein the pressure applied to the brachial artery is distributed substantially equally along the brachial artery.

7. A method for measuring systolic and diastolic blood pressure of a patient as defined in claim 6, wherein the first acoustic sensor is supported by a support contacting the patient's skin, the support having a surface area for contacting the patient's skin being sufficiently large for substantially reducing pressure exerted by the support onto the brachial artery due to inflation of the pressure cuff.

8. A method for measuring systolic and diastolic blood pressure of a patient as defined in claim 1, wherein the Korotkoff sound pulses are detected using a peak discriminator.

9. A method for measuring systolic and diastolic blood pressure of a patient as defined in claim 8, wherein peaks greater than a floor noise level are isolated.

10. A method for measuring systolic and diastolic blood pressure of a patient as defined in claim 9, wherein peaks not satisfying periodicity and constancy in repetition are discarded.

11. A method for measuring systolic and diastolic blood pressure of a patient as defined in claim 10, wherein peaks corresponding to Korotkoff sound pulses not perceptible to an average human ear are discarded.

12. A method for measuring systolic and diastolic blood pressure of a patient as defined in claim 10, comprising the step of determining a heart rate from the detected Korotkoff sound pulses.

13. A method for measuring systolic and diastolic blood pressure of a patient as defined in claim 12, comprising the step of updating the heart rate with each pulse found during searching for the systolic and diastolic pressure.

14. A method for measuring systolic and diastolic blood pressure of a patient as defined in claim 13, comprising the step of tracking gaps in a sequence of detected Korotkoff sound pulses.

15. A method for measuring systolic and diastolic blood pressure of a patient as defined in claim 14, comprising the step of determining a new value for the systolic and diastolic blood pressures if a new sequence of Korotkoff sound pulses is found.

16. A device for measuring systolic and diastolic blood pressure of a patient in an environment with extreme levels of noise and vibration, the device comprising:

a pressure cuff for being wrapped around a limb of the patient for applying pressure to a brachial artery of the patient, the pressure cuff having a first surface for being in contact with skin of the patient's limb and a second surface opposite the first surface for facing away from the skin of the patient's limb;

a pressure transducer for sensing the pressure applied to the brachial artery and for providing a pressure signal in dependence thereupon;

a first acoustic sensor for placement on the skin of the patient's limb over the brachial artery for sensing blood pressure signals corresponding to Korotkoff sounds and for producing a first acoustic signal in dependence thereupon;

a second acoustic sensor attached to the second surface and acoustically isolated therefrom for sensing noise and vibration and for producing a second acoustic signal in dependence thereupon; and, a processor for processing the first acoustic signal and the second acoustic signal using adaptive interference cancellation, for detecting Korotkoff sound pulses within the processed first acoustic signal and for determining systolic and diastolic blood pressure using the detected Korotkoff sound pulses and the pressure signal.

17. A device for measuring systolic and diastolic blood pressure of a patient as defined in claim 16, wherein the second acoustic sensor is attached to the second surface approximately diametrically opposite to the location of the first acoustic sensor with respect to the patient's limb.

18. A device for measuring systolic and diastolic blood pressure of a patient as defined in claim 17, wherein the second acoustic sensor is attached to the second surface at an upstream end of the pressure cuff with respect to the blood flow in the brachial artery.

19. A device for measuring systolic and diastolic blood pressure of a patient as defined in claim 16, comprising an array of first acoustic sensors for placement on the skin of the patient's limb across the brachial artery.

20. A device for measuring systolic and diastolic blood pressure of a patient as defined in claim 19, wherein the array of first acoustic sensors is housed in a bell shaped housing using an acoustic isolator.

21. A device for measuring systolic and diastolic blood pressure of a patient as defined in claim 20, wherein the second acoustic sensor is housed in a bell shaped housing using an acoustic isolator.

22. A device for measuring systolic and diastolic blood pressure of a patient as defined in claim 21, wherein the second acoustic sensor is removably attached to the second surface.

23. A device for measuring systolic and diastolic blood pressure of a patient as defined in claim 16, wherein the first acoustic sensor is housed in a bell shaped housing using an acoustic isolator.

24. A device for measuring systolic and diastolic blood pressure of a patient as defined in claim 23 wherein the first acoustic sensor is attached to the first surface.

25. A device for measuring systolic and diastolic blood pressure of a patient as defined in claim 24, wherein the pressure applied to the brachial artery is distributed substantially equally along the brachial artery.

26. A device for measuring systolic and diastolic blood pressure of a patient as defined in claim 25, wherein the bell shaped housing has a surface area for contacting the patient's skin being sufficiently large for substantially reducing pressure exerted by the bell onto the brachial artery due to inflation of the pressure cuff.

27. A device for measuring systolic and diastolic blood pressure of a patient as defined in claim 16, wherein the pressure cuff comprises a non inflatable extension for attaching the first acoustic sensor thereto.

28. A device for measuring systolic and diastolic blood pressure of a patient in an environment with extreme levels of noise and vibration, the device comprising:

a pressure cuff for being wrapped around a limb of the patient for applying pressure to a brachial artery of the patient, the pressure cuff having a first surface for being in contact with skin of the patient's limb and a second surface opposite the first surface for facing away from the skin of the patient's limb;

a pressure transducer for sensing the pressure applied to the brachial artery and for providing a pressure signal in dependence thereupon;

a first acoustic sensor attached to the first surface for placement on the skin of the patient's limb over the brachial artery at a downstream end of the pressure cuff with respect to the blood flow in the brachial artery for sensing blood pressure signals corresponding to Korotkoff sounds and for producing a first acoustic signal in dependence thereupon;

a second acoustic sensor attached to the second surface and acoustically isolated therefrom for sensing noise and vibration and for producing a second acoustic signal in dependence thereupon, the second acoustic sensor being attached approximately opposite to the location of the first acoustic sensor with respect to the patient's limb at an upstream end of the pressure cuff; and, a processor for processing the first acoustic signal and the second acoustic signal using adaptive interference cancellation, for detecting Korotkoff sound pulses within the processed first acoustic signal and for determining systolic and diastolic blood pressure using the detected Korotkoff sound pulses and the pressure signal.

\* \* \* \* \*